(12) United States Patent
Vokal

(10) Patent No.: US 6,504,078 B2
(45) Date of Patent: Jan. 7, 2003

(54) LEG GUARD AND METHOD FOR LEG INCISIONS

(75) Inventor: Donald Vokal, 668 Paradise Island Dr., DeFuniak Springs, FL (US) 32433

(73) Assignee: Donald Vokal, Destin, FL (US)

( * ) Notice: Subject to any disclaimer, the term of this patent is extended or adjusted under 35 U.S.C. 154(b) by 0 days.

(21) Appl. No.: 09/850,372

(22) Filed: May 7, 2001

(65) Prior Publication Data

US 2002/0165473 A1 Nov. 7, 2002

(51) Int. Cl.[7] .............................................. A61F 13/00
(52) U.S. Cl. ......................... 602/42; 128/882; 128/888
(58) Field of Search ................................ 128/846, 882, 128/892, 888; 602/8, 23, 27, 28, 42; 606/213, 215, 216

(56) References Cited

U.S. PATENT DOCUMENTS

| | | | | |
|---|---|---|---|---|
| 392,157 A | * | 10/1888 | Lee | |
| 458,804 A | * | 9/1891 | Ellis | |
| 684,411 A | * | 10/1901 | Cook | |
| 2,018,517 A | * | 10/1935 | Fetter | |
| 3,898,679 A | * | 8/1975 | Whitehead | 2/22 |
| 4,038,989 A | * | 8/1977 | Romero-Sierra et al. | |
| 4,425,913 A | * | 1/1984 | Lewis | 128/877 |
| 4,436,088 A | * | 3/1984 | Finnieston | 602/20 |
| 4,520,806 A | * | 6/1985 | Miller | 602/6 |
| 5,259,835 A | * | 11/1993 | Clark et al. | |
| 5,297,294 A | * | 3/1994 | Washick | 2/22 |
| 5,842,475 A | * | 12/1998 | Duback et al. | 128/846 |
| 5,897,520 A | * | 4/1999 | Gerig | 602/23 |

* cited by examiner

Primary Examiner—Nicholas D. Lucchesi
Assistant Examiner—Lalita M Hamilton

(57) ABSTRACT

A leg guard and method that protect the area around an incision that is placed into the leg during heart by-pass surgery. The leg guard has a generally concave body member that has a central section and a pair of outer sections located on either side of the central section. The radius of curvature of the outer sections is greater than the radius of curvature of the central section. A strap extends between the outer sections for encompassing a user's leg and holding the body member thereonto. The body member is made from a hypoallergenic material and has at least one aeration hole therethrough. A resilient member may be attached to the outer periphery of each outer section.

7 Claims, 3 Drawing Sheets

LEG GUARD AND METHOD FOR LEG INCISIONS

BACKGROUND OF THE INVENTION

1. Field of the Invention

The present invention relates to a device and method that protect a user's leg at the area of incision resulting from retrieving veins from the area during heart by-pass surgery.

2. Background of the Prior Art

During a heart by-pass surgery, good veins are used to by-pass a bad spot on a vein within the heart. Blood is permanently detoured through the good view thereby eliminating potential problems that can be caused by blockage within the by-passed vein. Several such veins can be by-passed during a single heart by-pass procedure. Typically, the good veins are harvested from the patient's leg, either from the thigh or the calf or both, depending on the number of heart veins that are being bypassed.

One of the complications experienced by the patient during recovery from the heart by-pass procedure, relates to the areas of incision on the leg or legs from which the good veins were retrieved. The area around the incision, which incision can be on the order of 12 inches in length or longer, is shaved in order to perform a good and sterile incision. After the incision is stitched back up, the incision itself becomes very tender and sensitive. As the hair that was originally shaved prior to the incision, grows back relative course and brisley, the regrowing hair can cause substantial discomfort. This discomfort is exacerbated by wearing clothing over the incision and during sleep when the two legs come in substantial contact with each other. This discomfort is especially acute if both legs received an incision during the heart by-pass surgery. As the incision needs aeration in order to heal quickly and properly, placing of gauze or bandages over the incision is not desired.

Therefore, there exists a need in the art for a system that protects an incision on a leg of a patient from the discomforts caused by placing clothing over the incision and by the patient's two legs coming in contact with one another. Such a system must allow the incision to receive sufficient aeration in order to allow the incision to breath, thereby expediting the healing process. The system must be of relatively simple design and implementation and must not cause undue pain or discomfort to the patient.

SUMMARY OF THE INVENTION

The leg guard and method for leg incisions of the present invention addresses the aforementioned needs in the art. The present system protects an incision on a leg, either on the thigh or on the calf area, from the pain and discomfort that can be caused by clothing and by the patient's two legs coming together during sleep and during walking. The system allows sufficient air circulation about the incision so that the incision is properly aerated, and the system is relatively simple to design and implement. No undue pain or discomfort is experienced by the user of the present invention.

The leg guard and method for leg incisions of the present invention is comprised of a generally concave body member having a central section with a first radius of curvature and a first outer section having a first outer periphery, the first outer section located on a first side of the central section, and a second outer section having a second outer periphery, the second section located on an opposing second side of the central section, the first outer section and the second outer section each having a second radius of curvature that is greater than the first radius of curvature. A strap extends between the first outer section and the second outer section. The body member is placed onto a leg of a wearer such that the central section is positioned over an incision on the leg and the strap is secured around the leg for holding the body member in place secured to the leg. Sizing means are provided for adjusting the length of the strap. An aeration hole may pass through the body member. A first resilient member is attached to the first outer periphery of the first section and a second resilient member is attached to the second outer periphery of the second section. The first resilient member and the second resilient member may each be made from a hypoallergenic material. The first radius of curvature of the central section may be zero. The body member may be made from a hypoallergenic material, such as plastic.

BRIEF DESCRIPTION OF THE DRAWINGS

Similar reference numerals refer to similar parts throughout the several views of the drawings.

DESCRIPTION OF THE PREFERRED EMBODIMENT

Figure 1:
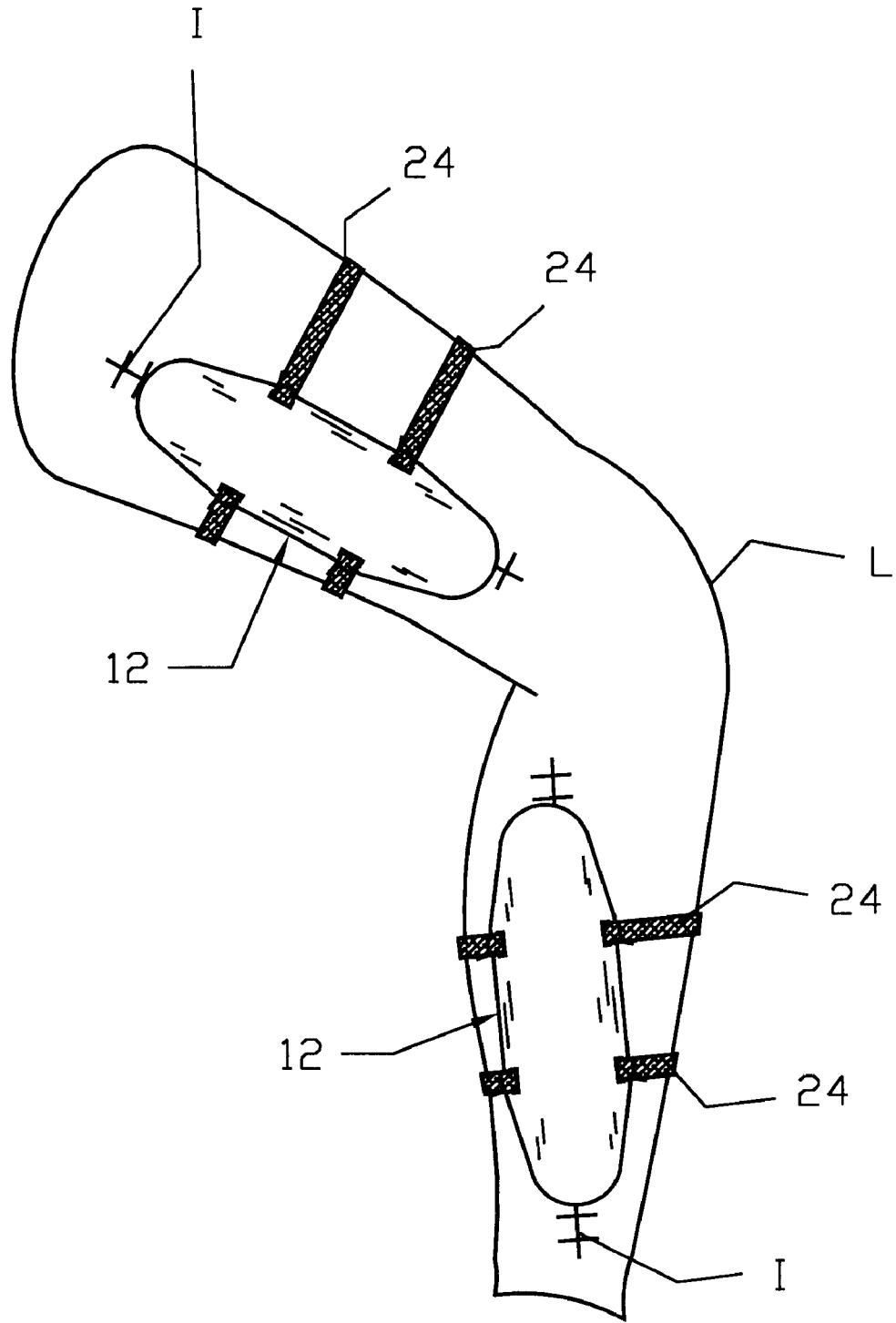
FIG. 1 is an environmental view of the leg guard and method for leg incisions of the present invention.
Figure 2A:
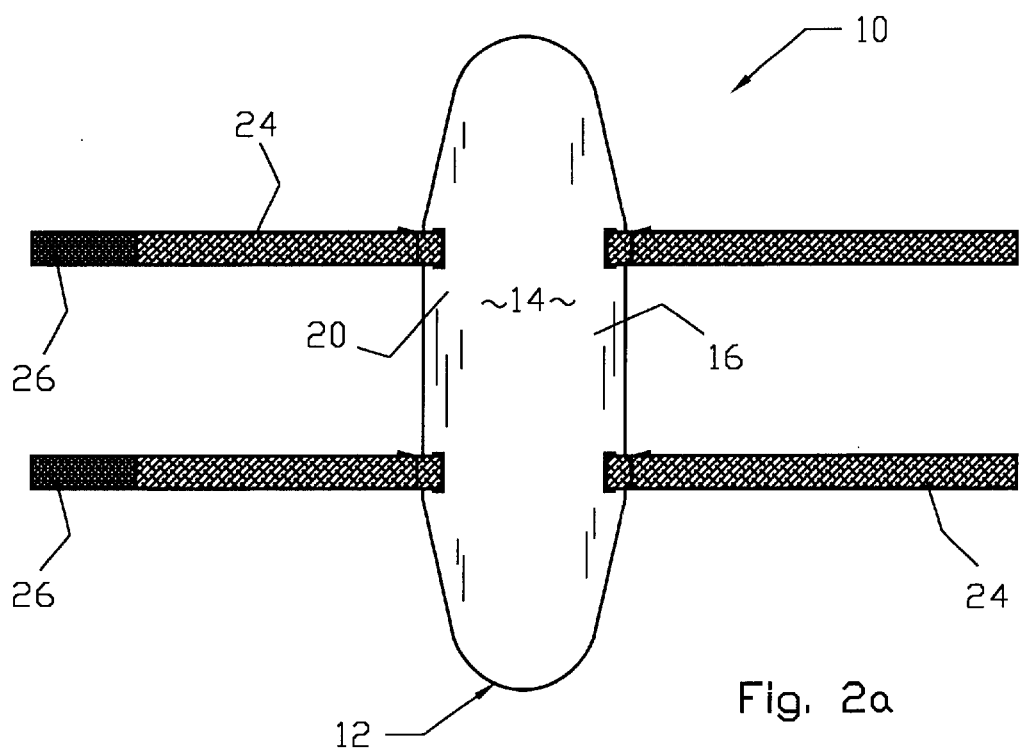
FIG. 2a is a top view of the leg guard employing a strap with a first type of sizing means.
Figure 2B:
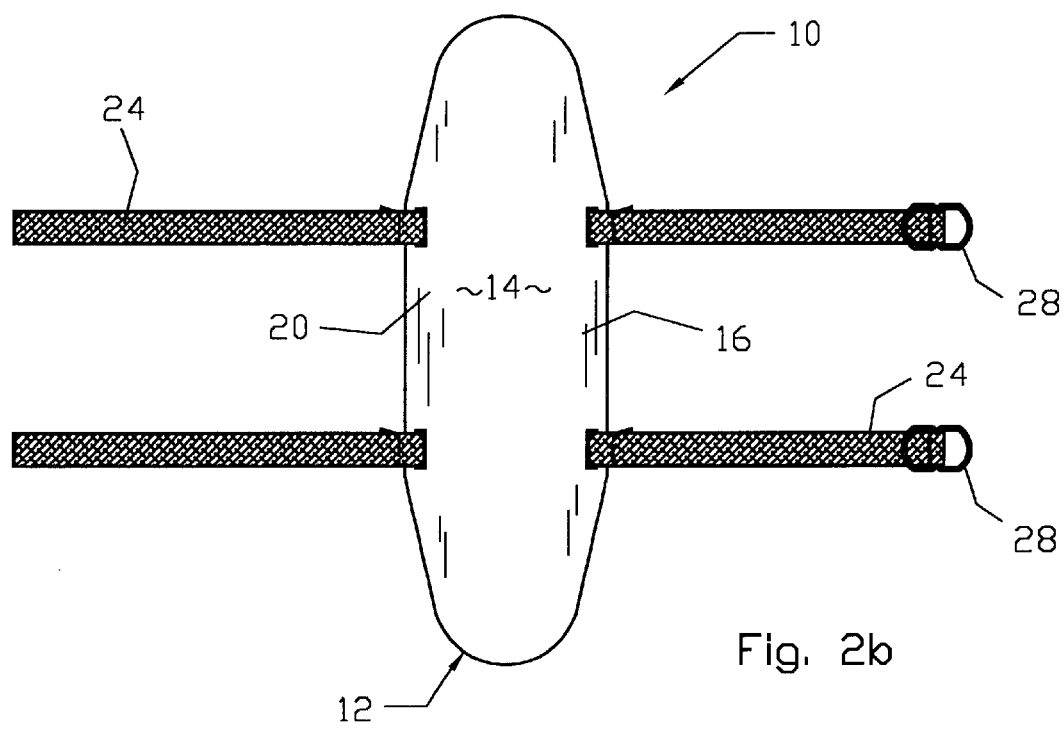
FIG. 2b is a top view of the leg guard employing a strap with a second type of sizing means.
Figure 4:
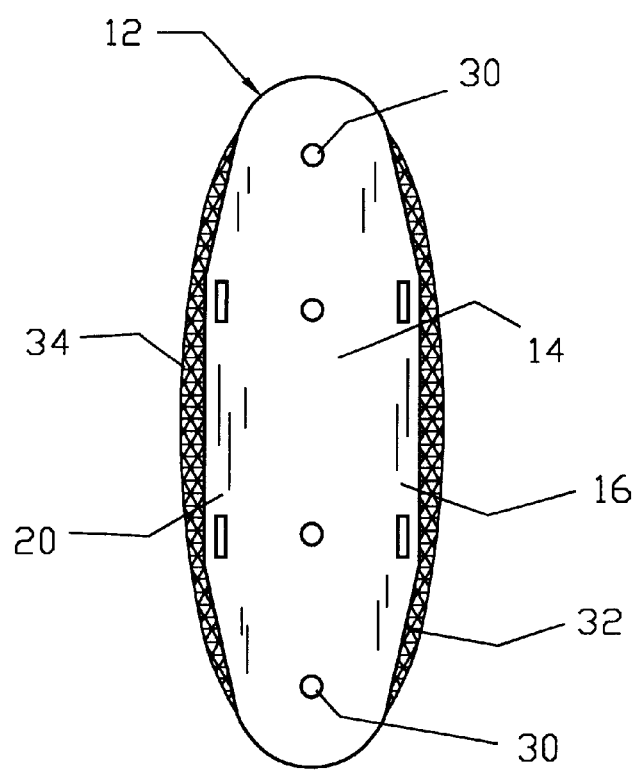
FIG. 4 is a bottom view of the leg guard.
Figure 3:
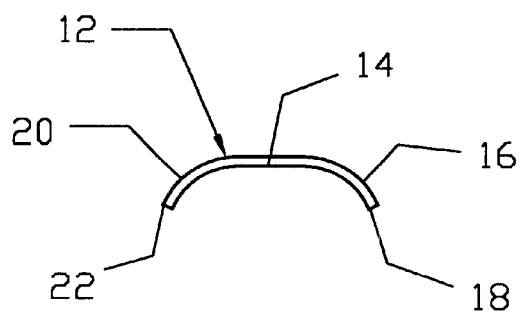
FIG. 3 is an end view of the leg guard.

Referring now to the drawings, it is seen that the leg guard and method for leg incisions of the present invention, generally denoted by reference numeral 10, is comprised of a generally concave body member 12 having a central section 14 with a first radius of curvature, a first outer section 16 having a first outer periphery 18, the first outer section 16 located on a first side of the central section 14, and a second outer section 20 having a second outer periphery 22, the second section. 20 located on an opposing second side of the central section 14, the first outer section 16 and the second outer section 20 each having a second radius of curvature that is greater than the first radius of curvature of the central section 14.

A strap 24 extends between the first outer section 16 and the second outer section 20. The strap 24 can be of any appropriate design and can be in one section that fixedly attaches to one of the outer sections 16 or 20, and removably attaches to the other outer section 20 or 16. The strap 24 can be fixedly attached to both outer sections 16 and 20 and can be made from an appropriate elastic material for sizing purposes, or, as seen, the strap can be in the two sections, each section attached to a respective one of the outer sections 16 and 20, with sizing means (including attachment means for the two sections) provided for adjusting the length of the strap 24, the sizing means being of any convention strap sizing method known in the art such as cooperating hook and loop material 26 being placed on each strap section, adjustment buckles 28 attached to the strap 24, etc.

The body member 12 is placed onto a leg L of a wearer such that the central section 14 is positioned over an incision I on the leg and the strap 24 is secured around the leg L for holding the body member 12 in place secured to the leg L, the strap 24 being sized appropriately. As the radius of curvature of the two outer sections 16 and 20 is greater than the radius of curvature of the central section 14, the central section 14 will be located some distance above the incision I when the device 10 is secured to the user's leg. As such, a passage will exist between the device 10 and the user's leg L allowing for circulation of air through the passage and thus over the incision I in order to provide sufficient aeration of the incision I. In addition, an aeration hole 30 may pass through the body member 12. A first resilient member 32 is attached to the first outer periphery 18 of the first section 16 and a second resilient member 34 is attached to the second outer periphery 22 of the second section 20. The first resilient member 32 and the second resilient member 34 are each made from a relatively soft material such as open or closed cell foam, rubber, neoprene, etc., and each may be hypoallergenic material. The first radius of curvature of the central section 14 may be zero. The body member 12 may be made from a hypoallergenic material.

In order to use the leg guard 10 of the present invention, a patient undergoes heart by-pass surgery and has an incision L placed into his leg L and has the incision I stitched appropriately. The body member 12 is positioned over the incision I such that the central section 14 is over top the incision I. The strap 24 is placed around the patient's leg L and secures the body member 12 to the leg L. If used, the resilient members 32 and 34 prevent the outer peripheries 18 and 22 of the two outer sections 16 and 20, respectively, from causing discomfort to the user. By using a hypoallergenic body member 12, or resilient members 32 and 34, if used, adverse reactions to patients with sensitive skin will not occur. The aeration holes 30 located on the body member 12 allow additional air to get to the incision I in order to foster quick healing.

While the invention has been particularly shown and described with reference to an embodiment thereof, it will be appreciated by those skilled in the art that various changes in form and detail may be made without departing from the spirit and scope of the invention.

I claim:

1. A method of protecting a human limb comprising the steps of:

placing an incision into the limb;

closing the incision;

providing a rigid and generally concave body member having a central section with a first radius of curvature and a first outer section having a first outer periphery, the first outer section located on a first side of the central section and a second outer section having a second outer periphery, the second section located on an opposing second side of the central section, the first outer section and the second outer section each having a second radius or curvature that is greater than the first radius of curvature;

providing a strap and extending the strap between the first outer section and the second outer section; and placing the body member onto the limb such that the central section is over the incision and securing the strap around the limb for holding the body member in place secured to the limb and not in contact with the incision.

2. The method as in claim 1 wherein the strap has sizing means for adjusting the length of the strap.

3. The method as in claim 1 wherein the body member has an aeration hole passing therethrough.

4. The method as in claim 1 further comprising the steps of:

providing a first resilient member and attaching the first resilient member to the first outer periphery of the first section; and providing a second resilient member and attaching the resilient member to the second outer periphery of the second section.

5. The method as in claim 4 wherein the first resilient member and the second resilient member are each made from a hypoallergenic material.

6. The method as in claim 1 wherein the first radius of curvature is zero.

7. The method as in claim 1 wherein the body member is made from a hypoallergenic material.

* * * * *